United States Patent
Young et al.

(10) Patent No.: US 7,887,562 B2
(45) Date of Patent: *Feb. 15, 2011

(54) TISSUE OPENING OCCLUDER

(75) Inventors: Michelle M. Young, Ham Lake, MN (US); Jana F. Oman, Spring Lake Park, MN (US); Paul R. Barratt, Minneapolis, MN (US)

(73) Assignee: EV3 Endovascular, Inc., Plymouth, MN (US)

( * ) Notice: Subject to any disclaimer, the term of this patent is extended or adjusted under 35 U.S.C. 154(b) by 241 days.

This patent is subject to a terminal disclaimer.

(21) Appl. No.: 11/927,448

(22) Filed: Oct. 29, 2007

(65) Prior Publication Data

US 2008/0058866 A1   Mar. 6, 2008

Related U.S. Application Data

(63) Continuation of application No. 10/209,797, filed on Jul. 30, 2002, now Pat. No. 7,288,105.

(60) Provisional application No. 60/309,337, filed on Aug. 1, 2001, provisional application No. 60/309,376, filed on Aug. 1, 2001, provisional application No. 60/309,418, filed on Aug. 1, 2001.

(51) Int. Cl.
    *A61B 17/04* (2006.01)
(52) U.S. Cl. ..................................... 606/213
(58) Field of Classification Search .......... 606/108, 606/200, 213, 215–218, 221, 232, 151–155, 606/75–78, 156, 157; 623/23.72; 128/899, 128/887

See application file for complete search history.

(56) References Cited

U.S. PATENT DOCUMENTS

| 2,307,480 A | 1/1943 | Ashe |
| 2,570,465 A | 2/1951 | Lundholm |
| 3,123,077 A | 3/1964 | Alcamo |
| 3,124,136 A | 3/1964 | Usher |
| 3,166,072 A | 1/1965 | Sullivan, Jr. |
| 3,646,615 A | 3/1972 | Ness |

(Continued)

FOREIGN PATENT DOCUMENTS

EP   0 317 406 A1   4/1989

(Continued)

OTHER PUBLICATIONS

U.S. Appl. No. 11/584,828, filed Oct. 23, 2006; Office Action sent Jun. 29, 2007.

(Continued)

*Primary Examiner*—Anhtuan T Nguyen
*Assistant Examiner*—Elizabeth Houston
(74) *Attorney, Agent, or Firm*—Knobbe Martens Olson & Bear LLP (57) ABSTRACT

A tissue opening occluder comprising first and second occluder portions, each occluder portion including a frame structure and an attachment structure to attach one portion to the other portion. The frames may be utilized to constrain the tissue between the two portions enough to restrict the significant passage of blood therethrough. The frame portions may be covered by a fabric suspended from a perimeter thereof. The occluder portions are conjoined at least one point on each portion.

19 Claims, 7 Drawing Sheets

U.S. PATENT DOCUMENTS

| | | |
|---|---|---|
| 3,716,058 A | 2/1973 | Tanner, Jr. |
| 3,874,388 A | 4/1975 | King et al. |
| 3,892,232 A | 7/1975 | Neufeld |
| 4,006,747 A | 2/1977 | Kronenthal et al. |
| 4,007,743 A | 2/1977 | Blake |
| 4,060,089 A | 11/1977 | Noiles |
| 4,532,926 A | 8/1985 | O'Holla |
| 4,669,473 A | 6/1987 | Richards et al. |
| 4,688,561 A | 8/1987 | Reese |
| 4,781,177 A | 11/1988 | Lehigot |
| 4,836,204 A | 6/1989 | Landymore et al. |
| 4,873,976 A | 10/1989 | Schreiber |
| 4,884,572 A | 12/1989 | Bays et al. |
| 4,895,148 A | 1/1990 | Bays et al. |
| 4,917,089 A | 4/1990 | Sideris |
| 4,924,865 A | 5/1990 | Bays et al. |
| 4,935,028 A | 6/1990 | Drews |
| 4,976,715 A | 12/1990 | Bays et al. |
| 5,013,316 A | 5/1991 | Goble et al. |
| 5,021,059 A | 6/1991 | Kensey et al. |
| 5,053,047 A | 10/1991 | Yoon |
| 5,059,206 A | 10/1991 | Winters |
| 5,085,661 A | 2/1992 | Moss |
| 5,102,421 A | 4/1992 | Anspach, Jr. |
| 5,108,420 A | 4/1992 | Marks |
| 5,129,906 A | 7/1992 | Ross et al. |
| 5,171,259 A | 12/1992 | Inoue |
| 5,192,301 A | 3/1993 | Kamiya et al. |
| 5,203,864 A | 4/1993 | Phillips |
| 5,236,431 A | 8/1993 | Gogolewski et al. |
| 5,246,441 A | 9/1993 | Ross et al. |
| 5,254,133 A | 10/1993 | Seid |
| 5,258,000 A | 11/1993 | Gianturco |
| 5,261,914 A | 11/1993 | Warren |
| 5,284,488 A | 2/1994 | Sideris |
| 5,334,217 A | 8/1994 | Das |
| 5,342,393 A | 8/1994 | Stack |
| 5,350,399 A | 9/1994 | Erlebacher et al. |
| 5,356,432 A | 10/1994 | Rutkow et al. |
| 5,380,334 A | 1/1995 | Torrie et al. |
| 5,397,331 A | 3/1995 | Himpens et al. |
| 5,400,805 A | 3/1995 | Warren |
| 5,425,744 A | 6/1995 | Fagan et al. |
| 5,433,727 A | 7/1995 | Sideris |
| 5,451,235 A * | 9/1995 | Lock et al. .................. 606/213 |
| 5,470,337 A | 11/1995 | Moss |
| 5,486,193 A | 1/1996 | Bourne et al. |
| 5,505,735 A | 4/1996 | Li |
| 5,507,811 A | 4/1996 | Koike et al. |
| 5,562,704 A | 10/1996 | Tamminmäki et al. |
| 5,578,045 A | 11/1996 | Das |
| 5,582,616 A | 12/1996 | Bolduc et al. |
| 5,601,571 A | 2/1997 | Moss |
| 5,620,461 A | 4/1997 | Muijs Van De Moer et al. |
| 5,634,936 A | 6/1997 | Linden et al. |
| 5,643,317 A | 7/1997 | Pavcnik et al. |
| 5,649,950 A | 7/1997 | Bourne et al. |
| 5,662,681 A | 9/1997 | Nash et al. |
| 5,662,683 A | 9/1997 | Kay |
| 5,702,421 A | 12/1997 | Schneidt |
| 5,709,707 A | 1/1998 | Lock et al. |
| 5,725,552 A | 3/1998 | Kotula et al. |
| 5,728,116 A | 3/1998 | Rosenman |
| 5,733,294 A | 3/1998 | Forber et al. |
| 5,741,297 A | 4/1998 | Simon |
| 5,792,179 A | 8/1998 | Sideris |
| 5,797,960 A | 8/1998 | Stevens et al. |
| 5,810,846 A | 9/1998 | Virnich et al. |
| 5,823,956 A | 10/1998 | Roth et al. |
| 5,827,298 A | 10/1998 | Hart et al. |
| 5,829,447 A | 11/1998 | Stevens et al. |
| 5,843,084 A | 12/1998 | Hart et al. |
| 5,846,261 A | 12/1998 | Kotula et al. |
| 5,853,422 A | 12/1998 | Huebsch et al. |
| 5,855,614 A | 1/1999 | Stevens et al. |
| 5,860,948 A | 1/1999 | Buscemi |
| 5,861,003 A | 1/1999 | Latson et al. |
| 5,879,366 A | 3/1999 | Shaw et al. |
| 5,893,850 A | 4/1999 | Cachia |
| 5,902,317 A | 5/1999 | Kleshinski et al. |
| 5,904,703 A | 5/1999 | Gilson |
| 5,919,200 A | 7/1999 | Stambaugh et al. |
| 5,944,738 A | 8/1999 | Amplatz et al. |
| 5,947,997 A | 9/1999 | Pavcnik et al. |
| 5,976,174 A | 11/1999 | Ruiz |
| 5,980,524 A | 11/1999 | Justin et al. |
| 6,024,756 A | 2/2000 | Huebsch et al. |
| 6,059,823 A | 5/2000 | Holman et al. |
| 6,077,281 A | 6/2000 | Das |
| 6,077,291 A * | 6/2000 | Das .......................... 606/213 |
| 6,079,414 A | 6/2000 | Roth |
| 6,080,182 A | 6/2000 | Shaw et al. |
| 6,087,552 A | 7/2000 | Gregory |
| 6,096,052 A | 8/2000 | Callister et al. |
| 6,106,532 A | 8/2000 | Koike et al. |
| 6,110,212 A | 8/2000 | Gregory |
| 6,123,715 A | 9/2000 | Amplatz |
| 6,152,144 A | 11/2000 | Lesh et al. |
| 6,156,055 A | 12/2000 | Ravenscroft |
| 6,171,329 B1 | 1/2001 | Shaw et al. |
| 6,174,322 B1 | 1/2001 | Schneidt |
| 6,190,400 B1 | 2/2001 | Van De Moer et al. |
| 6,200,336 B1 | 3/2001 | Pavcnik et al. |
| 6,206,895 B1 | 3/2001 | Levinson |
| 6,206,907 B1 | 3/2001 | Marino et al. |
| 6,210,338 B1 | 4/2001 | Afremov et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,231,589 B1 | 5/2001 | Wessman et al. |
| 6,238,416 B1 | 5/2001 | Sideris |
| 6,241,747 B1 | 6/2001 | Ruff |
| 6,245,079 B1 | 6/2001 | Nobles et al. |
| 6,270,515 B1 | 8/2001 | Linden et al. |
| 6,277,140 B2 | 8/2001 | Ginn et al. |
| 6,280,460 B1 | 8/2001 | Bolduc et al. |
| 6,290,674 B1 | 9/2001 | Roue et al. |
| 6,290,702 B1 | 9/2001 | Fucci et al. |
| 6,296,641 B2 | 10/2001 | Burkhead et al. |
| 6,299,597 B1 | 10/2001 | Buscemi et al. |
| 6,306,177 B1 | 10/2001 | Felt et al. |
| 6,312,446 B1 | 11/2001 | Huebsch et al. |
| 6,319,263 B1 | 11/2001 | Levinson |
| 6,319,270 B1 | 11/2001 | Grafton et al. |
| 6,319,276 B1 | 11/2001 | Holman et al. |
| 6,322,563 B1 | 11/2001 | Cummings et al. |
| 6,328,727 B1 | 12/2001 | Frazier et al. |
| 6,334,864 B1 | 1/2002 | Amplatz et al. |
| 6,342,064 B1 | 1/2002 | Koike et al. |
| 6,346,074 B1 | 2/2002 | Roth |
| 6,348,053 B1 | 2/2002 | Cachia |
| 6,355,052 B1 | 3/2002 | Neuss et al. |
| 6,368,339 B1 | 4/2002 | Amplatz |
| 6,375,671 B1 | 4/2002 | Kobayashi et al. |
| 6,379,368 B1 | 4/2002 | Corcoran et al. |
| 6,391,048 B1 | 5/2002 | Ginn et al. |
| 6,419,669 B1 | 7/2002 | Frazier et al. |
| 6,440,152 B1 | 8/2002 | Gainor et al. |
| 6,458,100 B2 | 10/2002 | Roue et al. |
| 6,461,364 B1 | 10/2002 | Ginn et al. |
| 6,468,303 B1 | 10/2002 | Amplatz et al. |
| 6,485,504 B1 | 11/2002 | Johnson et al. |
| 6,508,828 B1 | 1/2003 | Akerfeldt et al. |
| 6,517,564 B1 | 2/2003 | Grafton et al. |

| | | |
|---|---|---|
| 6,533,762 B2 | 3/2003 | Kanner |
| 6,537,299 B1 | 3/2003 | Hogendijk et al. |
| 6,537,300 B2 * | 3/2003 | Girton .................... 606/213 |
| 6,551,343 B1 | 4/2003 | Törmälä et al. |
| 6,551,344 B2 | 4/2003 | Thill |
| 6,569,188 B2 | 5/2003 | Grafton et al. |
| 6,596,014 B2 | 7/2003 | Levinson et al. |
| 6,623,508 B2 | 9/2003 | Shaw et al. |
| 6,626,917 B1 | 9/2003 | Craig |
| 6,632,238 B2 | 10/2003 | Ginn et al. |
| 6,635,066 B2 | 10/2003 | Tanner et al. |
| 6,645,225 B1 | 11/2003 | Atkinson |
| 6,656,206 B2 | 12/2003 | Corcoran et al. |
| 6,663,633 B1 | 12/2003 | Pierson, III |
| 6,695,867 B2 | 2/2004 | Ginn et al. |
| 6,702,835 B2 | 3/2004 | Ginn |
| 6,712,836 B1 | 3/2004 | Berg et al. |
| 6,719,777 B2 | 4/2004 | Ginn et al. |
| 6,776,784 B2 | 8/2004 | Ginn |
| 6,911,037 B2 | 6/2005 | Gainor et al. |
| 7,288,105 B2 | 10/2007 | Oman et al. |
| 7,377,936 B2 | 5/2008 | Gainor et al. |
| 7,479,155 B2 | 1/2009 | Gainor et al. |
| 7,582,103 B2 | 9/2009 | Young et al. |
| 7,780,700 B2 | 8/2010 | Frazier et al. |
| 2001/0014800 A1 | 8/2001 | Frazier et al. |
| 2001/0021872 A1 | 9/2001 | Bailey et al. |
| 2001/0023332 A1 | 9/2001 | Hahnen |
| 2001/0031973 A1 | 10/2001 | Nobles et al. |
| 2001/0034537 A1 | 10/2001 | Shaw et al. |
| 2001/0037129 A1 | 11/2001 | Thill |
| 2001/0039434 A1 | 11/2001 | Frazier et al. |
| 2001/0039435 A1 | 11/2001 | Roue et al. |
| 2001/0039436 A1 | 11/2001 | Frazier et al. |
| 2001/0039450 A1 | 11/2001 | Pavcnik et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0055767 A1 | 5/2002 | Forde et al. |
| 2002/0068950 A1 | 6/2002 | Corcoran et al. |
| 2002/0165574 A1 | 11/2002 | Ressemann et al. |
| 2002/0165598 A1 | 11/2002 | Wahr et al. |
| 2002/0169475 A1 | 11/2002 | Gainor et al. |
| 2002/0183786 A1 | 12/2002 | Girton |
| 2002/0183787 A1 | 12/2002 | Wahr et al. |
| 2002/0198563 A1 | 12/2002 | Gainor et al. |
| 2003/0023262 A1 | 1/2003 | Welch |
| 2003/0028213 A1 | 2/2003 | Thill et al. |
| 2003/0045893 A1 | 3/2003 | Ginn |
| 2003/0050600 A1 | 3/2003 | Ressemann et al. |
| 2003/0050665 A1 | 3/2003 | Ginn |
| 2003/0055455 A1 | 3/2003 | Yang et al. |
| 2003/0144694 A1 | 7/2003 | Chanduszko et al. |
| 2003/0144695 A1 | 7/2003 | McGuckin, Jr. et al. |
| 2003/0191495 A1 | 10/2003 | Ryan et al. |
| 2003/0195530 A1 | 10/2003 | Thill |
| 2003/0208232 A1 | 11/2003 | Blaeser et al. |
| 2003/0225421 A1 * | 12/2003 | Peavey et al. ............. 606/151 |
| 2004/0039414 A1 | 2/2004 | Carley et al. |
| 2004/0073236 A1 | 4/2004 | Carley et al. |
| 2004/0073242 A1 | 4/2004 | Chanduszko |
| 2004/0092973 A1 | 5/2004 | Chanduszko et al. |
| 2004/0098121 A1 | 5/2004 | Opolski |
| 2004/0127917 A1 | 7/2004 | Ginn |
| 2004/0133236 A1 | 7/2004 | Chanduszko |
| 2004/0176788 A1 | 9/2004 | Opolski |
| 2004/0193194 A1 | 9/2004 | Laufer |
| 2004/0220596 A1 | 11/2004 | Frazier et al. |
| 2004/0243122 A1 | 12/2004 | Auth et al. |
| 2004/0249398 A1 | 12/2004 | Ginn |
| 2004/0267191 A1 | 12/2004 | Gifford, III et al. |
| 2005/0033327 A1 | 2/2005 | Gainor et al. |
| 2005/0059984 A1 | 3/2005 | Chanduszko |
| 2005/0119675 A1 | 6/2005 | Adams et al. |
| 2005/0187568 A1 | 8/2005 | Klenk et al. |
| 2005/0192626 A1 | 9/2005 | Widomski et al. |
| 2005/0251201 A1 | 11/2005 | Roue et al. |
| 2007/0106327 A1 | 5/2007 | Thill et al. |
| 2007/0112382 A1 | 5/2007 | Thill et al. |
| 2008/0195123 A1 | 8/2008 | Gainor et al. |

FOREIGN PATENT DOCUMENTS

| | | |
|---|---|---|
| EP | 0 362 113 A1 | 4/1990 |
| EP | 0 474 887 A1 | 3/1992 |
| EP | 0 632 999 A1 | 1/1995 |
| EP | 0 655 222 B1 | 6/1998 |
| EP | 0 541 063 B1 | 9/1998 |
| EP | 0 876 793 A2 | 11/1998 |
| EP | 0 920 842 A1 | 6/1999 |
| EP | 0 545 091 B1 | 7/1999 |
| EP | 1 046 375 A1 | 10/2000 |
| EP | 0 793 457 B1 | 10/2001 |
| EP | 1 214 911 A1 | 6/2002 |
| EP | 1 281 355 A2 | 2/2003 |
| FR | 1 317 354 | 1/1963 |
| GB | 2 269 321 | 2/1994 |
| JP | 7171173 | 7/1995 |
| JP | 8141070 | 6/1996 |
| JP | 8196623 | 8/1996 |
| WO | WO 85/03857 | 9/1985 |
| WO | WO 89/01767 | 3/1989 |
| WO | WO 90/14796 | 12/1990 |
| WO | WO 93/13712 | 7/1993 |
| WO | WO 93/14705 | 8/1993 |
| WO | WO 95/28885 | 11/1995 |
| WO | WO 96/32882 | 10/1996 |
| WO | WO 97/18762 | 5/1997 |
| WO | WO 97/41779 | 11/1997 |
| WO | WO 97/42878 | 11/1997 |
| WO | WO 98/08462 | 3/1998 |
| WO | WO 98/27868 | 7/1998 |
| WO | WO 99/07289 | 2/1999 |
| WO | WO 99/18862 | 4/1999 |
| WO | WO 99/18864 | 4/1999 |
| WO | WO 99/18871 | 4/1999 |
| WO | WO 99/38454 | 8/1999 |
| WO | WO 99/40849 | 8/1999 |
| WO | WO 00/56376 | 9/2000 |
| WO | WO 00/69365 | 11/2000 |
| WO | WO 01/17435 | 3/2001 |
| WO | WO 01/21246 | 3/2001 |
| WO | WO 01/30267 | 5/2001 |
| WO | WO 02/32496 | 4/2002 |
| WO | WO 02/38051 | 5/2002 |
| WO | WO 02/96295 | 12/2002 |
| WO | WO 02/098298 | 12/2002 |
| WO | WO 03/103476 | 12/2003 |

OTHER PUBLICATIONS

U.S. Appl. No. 11/607,237, filed Nov. 30, 2006; Office Action sent Jul. 12, 2007.

Office Action dated Nov. 25, 2003, European Patent Application No. 02 016 922.3-1265.

Office Action dated Jan. 1, 2005, European Patent Application No. 02 016 922.3-1265.

Ruiz, C. E. et al. "The Puncture Technique: A New Method for Transcatheter Closure of Patent Foramen Ovale," Cath. and Cardiovasc. Interv. 53:369-372 (2001).

Abstract of *Transcatheter Closure of Patent Foramen Ovale Using the Amplatzer Septal Occluder to Prevent Recurrence of Neurological Decompression Illness in Divers*, Heart Mar. 1999; 81(3):257-61.
*Atrial Septal Defect, Patent Foramen Ovale* by Michael A. Portman; published Apr. 15, 2002 in eMedicine Journal, vol. 3 No. 4.
Office Action dated Feb. 22, 2008: U.S. Appl. No. 11/607,237, U.S. Publication 2007-0112382 A1.

Extended European Search Report dated Aug. 29, 2008, European Patent Application No. 08152456.3 published as EP 1955661 in 5 pages.
Office Action dated Apr. 4, 2008: U.S. Appl. No. 11/584,828, U.S. Publication 2007-0106327 A1 in 12 pages.

* cited by examiner

TISSUE OPENING OCCLUDER

RELATED APPLICATIONS

This is a continuation application of U.S. patent application Ser. No. 10/209,797, filed Jul. 30, 2002, now U.S. Pat. No. 7,288,105, which claims benefit of U.S. Provisional Patent Application Ser. Nos. 60/309,337; 60/309,376; and 60/309,418; all having a filing date of Aug. 1, 2001, all of which are hereby incorporated by reference in their entirety.

BACKGROUND OF THE INVENTION

1. Field of the Invention

The present invention generally relates to devices for occluding a tissue opening such as a patent foramen ovale (PFO) or shunt in the heart, the vascular system, etc. and particularly provides an occluder device deliverable via a catheter to the site of a tissue opening.

2. Description of the Related Art

The device of the subject invention, in all its embodiments, may be utilized for the occlusion of many types of tissue openings, such as septal defects and PFO, and the like. For the sake of clarity, the present invention may, at times, be described specifically in the context of occlusion of a PFO. This specific description, however, should not be taken to limit the scope of the possible applications of the present invention.

The term "patent foramen ovale" generally refers to the failure to close a normal opening between the left and right atria (i.e., upper chambers) of the heart. Typically, a foramen ovale is a flap-like opening between the left and right atria of the heart which persists long after birth. Commonly, the foramen ovale has one flap extending from the top of the atrial chamber and another flap extending from the bottom of the atrial chamber, wherein the two flaps meet or overlap each other. Specifically, a PFO is typically located between the atrial septum primum and secundum at the location of the fossa ovalis. The opening provides a path to allow blood to bypass the lungs in an unborn infant, since the lungs are not in use during that period. The foramen ovale typically becomes functionally closed after the birth of the infant due to greater pressure from the increased blood flow in the left atrium acting upon the flap. However, in humans, for example, as many as 1 in 5 people have foramen ovale that do not fully close. In the absence of other cardiac defects or unusual cardiac pressures, the open foramen ovale does not present a substantial problem. However, in patients having circulatory problems-wherein the pressure on the right side of the heart is increased, for example as the result of congenital heart disease, blood may begin to flow through the foramen ovale. This result may also occur, for example, in divers when experiencing an increase in pressure due to being under water. The presence of a significantly large PFO, a flap structure that cannot provide sufficient seal, or a significant increase in pressure can cause blood to shunt across the defect from the right atrium to the left atrium and hence on to the left ventricle, aorta, and brain. If the defect is not closed, the risk of stroke is increased. Shunting of blood from the left to the right side can also have negative, consequences, such as cardiac failure or hemoptysis.

Tissue openings have traditionally been corrected by open heart surgery which required the surgeon to open the chest of a patient and bypass the heart temporarily. The surgeon would then physically cut into the heart and suture the opening closed. In the case of larger defects, a patch of a biologically compatible material would be sewn onto the tissue to cover the opening. However, the risk of complications occurring during such an intricate procedure presents substantial problems that patients would rather avoid.

In order to avoid such complications and the long recovery times associated with open heart surgery, a variety of trans-catheter closure techniques have been implemented. In such techniques, an occluding device is delivered through a catheter to the site of the tissue opening. Once the occlusion device is positioned adjacent the opening, it must be attached to the tissue wall containing the opening in a manner that permits it to effectively block the passage of blood through the opening. Furthermore, the occlusion device must also adjust to the anatomy or structure of the PFO, commonly a tunnel like structure, the width and length of which varies substantially between patients. As has been documented in the literature, the trans-catheter techniques developed thus far have had drawbacks associated therewith.

For example, a variety of heretofore known devices require assembly at the situs of the tissue opening. That is to say separable or separate halves of the device are deployed and subsequently united so as to traverse or span the tissue opening in furtherance of closure. Some well known devices require threading or "buttoning" of the discrete device elements. Additionally, such devices require special delivery and/or deployment tools, making their utility less than desirable.

A further shortcoming in the art yet to be adequately and fully addressed is the issue of device positioning at the situs and, more particularly, re-positioning in furtherance of effectuating a proper seal of the tissue opening. Also not addressed is the ability to retrieve the device from the situs without damage thereto. Heretofore, known devices appear to evidence a broad functionality, namely that of occlusion, or more pointedly, plugging a tissue opening without a full or more developed functionality of the constituents or substructures of the device, e.g., a device which includes a single occluder reversibly secured in place by an anchor assembly.

Heretofore known self expanding devices tend to be structurally complex, expensive to produce and cumbersome to load, unload, and reliably position at the situs of a tissue opening, and insensitive to the variable requirements of the PFO tunnel geometry. The balance or tension between the structural integrity of the device, its "size" (e.g., bulk, rigidity, etc.), and ability to remain optimally positioned continues to be a critical consideration, cardiac devices being subject to the rhythmic pumping of the heart, on the order of 100,000 beats per day.

The present invention addresses the needs of the field, as well as other problems associated with the prior art. The present invention offers advantages over the prior art and solves problems associated therewith.

SUMMARY OF THE INVENTION

The present invention is a tissue opening occluder which preferably has first and second portions. Both portions include a frame. One or both of the portions may have means for attaching the two portions together. Each of the frame portions is placed or positioned on one of opposite sides of a tissue wall to occlude the opening enough to restrict the significant passage of blood therethrough. One or both of the frame portions may also have a fabric support structure and have fabric suspended from a perimeter thereof. The fabric preferably is of such a type that it promotes the growth of tissue on the surface of or within the fabric. The portions may be directly attached together, attached by means of an attachment structure that is independent of either portion, may be conjoined at a single point or at a plurality of points, or may be attached by their frame and/or fabric elements. One or both of the portions may be formed in different shapes or may be identically configured.

In a first embodiment of the subject invention, the portions or halves of the occlusion device are configured as occluding panels, namely reversibly expandable elements which cooperatively engage opposing wall portions in the vicinity of the tissue defect (e.g., structures which are positioned in each atrium). Such occluding panels may be substantially planar or may have a significant third dimension. A variety of linkages are contemplated for integrating or otherwise joining the panels such that the sought after device responsiveness is obtained.

In a first alternate embodiment of the subject invention, one half of the occlusion device may be configured as an occluding panel (i.e., atrium engaging element), having two or three dimensions, while the second half may comprise a planar wire anchor structure which is configured to resiliently occupy a body structure, such as a PFO "tunnel," in furtherance of stabilizing the occluder panel portion of the device. The anchoring or positioning member may utilize one or more hook structures for engaging tissue surrounding the opening.

In yet a further embodiment of the subject invention, the device is adapted to be received and retained exclusively within the PFO "tunnel," no structure thereof extending into the atrium. The anchor structure stabilizes an occluding panel such that the panel "bridges" the portions of the septum within the area of the defect.

The present invention is thus an improved device over structures known in the prior art. More specific features and advantages obtained in view of those features will become apparent with reference to the drawing figures and DETAILED DESCRIPTION OF THE INVENTION.

DETAILED DESCRIPTION OF THE PREFERRED EMBODIMENT

As a preliminary matter, the subject invention contemplates three general configurations, several styles of each shown and subsequently described in the figures. The first general configuration for the tissue opening occluder (e.g., those illustrated in FIGS. 1-9) is characterized by paired occluder panels which are operatively joined so as to permit a high degree of motion, including rotation. The occluder panels are positioned within each atrium so as to "patch" (i.e., overlay) the septum in the vicinity of the defect, each occluder panel being in relative tension (i.e., being drawn towards each other). The second general configuration for the tissue opening occluder (e.g., that structure illustrated in FIGS. 10-23) is characterized by a single occluder panel, functioning in a similar capacity as heretofore described, anchored by a substantially planar wire structure positionable for retention within the "tunnel" of the PFO (i.e., overlapping septal portions). A third configuration for the tissue opening occluder (e.g., those illustrated in FIGS. 24-26) is characterized by its deployed, occluding position, specifically its retention within a defect such that the device is effectively contained within a tunnel of a PFO so as to greatly reduce, if not eliminate, passage (i.e., shunting) of blood from the right to left atrium. Finally, a variety of advantageous linkages, namely those of FIGS. 3-9, facilitating operative engagement between the major structural elements of the several embodiments, are provided.

Figure 1:
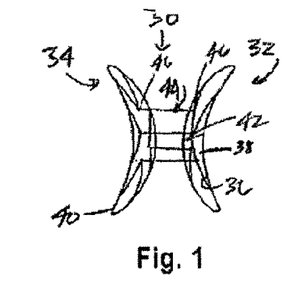
FIGS. 1 and 2 are side views of tissue opening occluders of the present invention, particularly illustrating the cooperative engagement of a pair of occluder panels.
Figure 2:
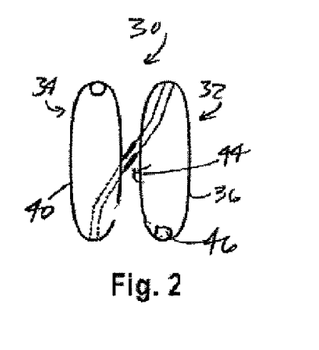
Figure 3:
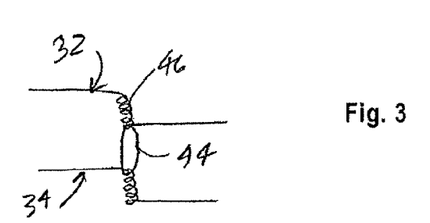
FIGS. 3-9 illustrate a representative variety of operative engagements contemplated for the structures of the present invention.
Figure 4:
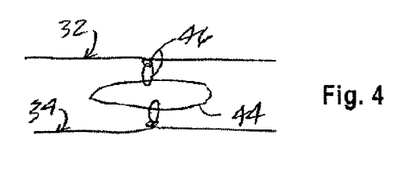
Figure 5:
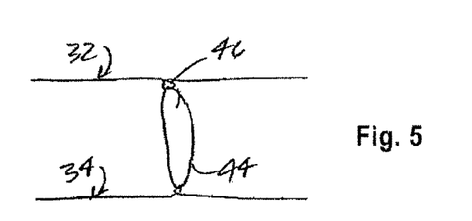
Figure 6:
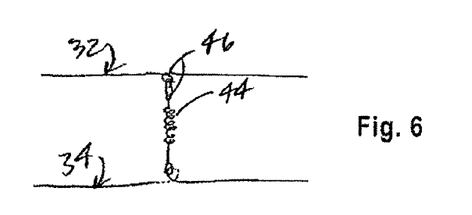
Figure 7:
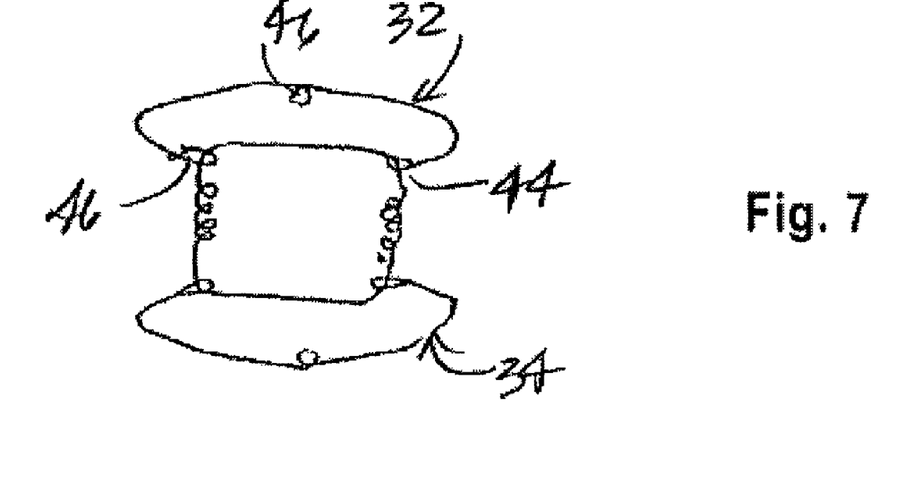
Figure 8:
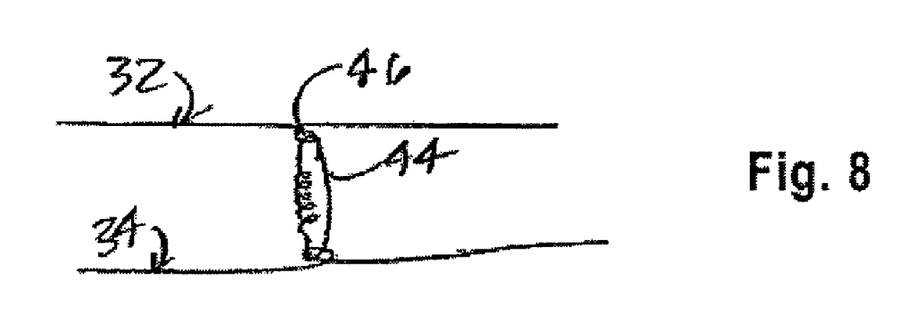
Figure 9:
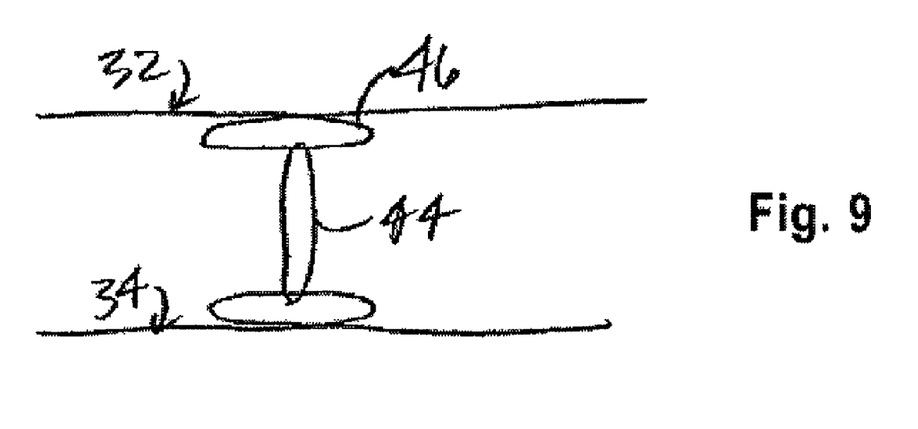
Figure 10:
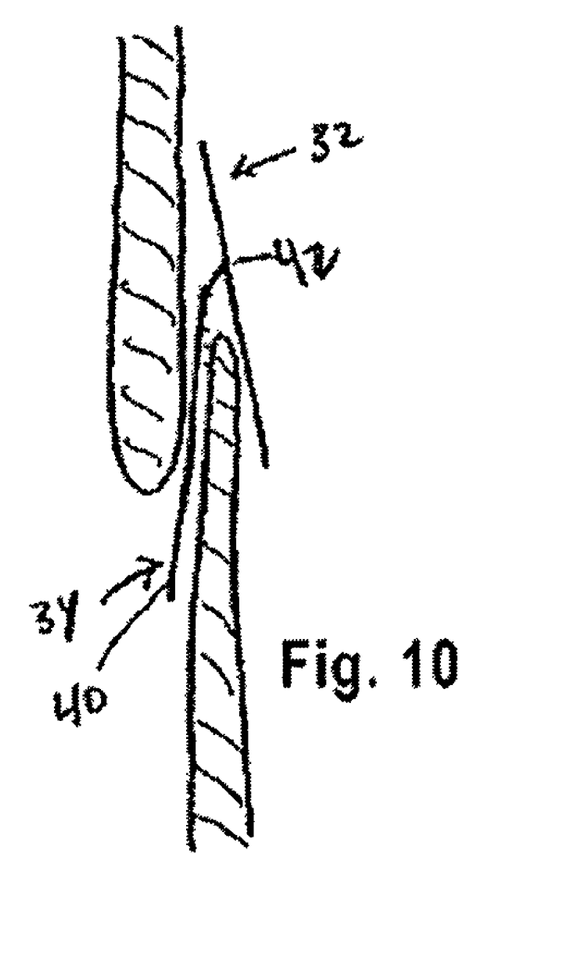
FIG. 10 illustrates a side view of an anchored occluder of the subject invention sealing a PFO.

Referring generally to FIGS. 1 and 2, there is illustrated a first general configuration for the subject reversibly deployable tissue opening occluder 30 which includes first and second portions, more particularly, an occluder panel 32 and an anchor assembly 34 extending therefrom, each of these structures being intended to be opposingly paired about a tissue opening of a type as illustrated in FIG. 10. The anchor assembly 34 of this general configuration comprises a panel similar to the occluder panel, however not necessarily identical therewith, which is joined, at least indirectly, to the occluder panel 32 via a linkage 44. The occluder panel 32 includes a fabric support structure 36 and fabric 38 supported by a perimeter thereof. The fabric support structure may include the wire frame, the linkage, or both. The wire frame can be of many shapes and is preferably made of superelastic wire, preferably Nitinol. The wire "frames preferably have a predetermined shape which is restored after deployment of the wire frame through a delivery catheter. The fabric is secured to the fabric support structure by suturing or other methods known in the art. The fabric is biocompatible and preferably supports tissue ingrowth so as to stabilize the implanted device at the implant site. Suitable fabrics include polyester, ePTFE, and other appropriate materials. Preferably, but not necessarily, the occluder panel 32 may embrace the panel styles disclosed in U.S. Pat. Nos. 6,214,029, 6,440,152, 6,551,344, each of which are incorporated herein by reference. As will be later detailed, once the occluder panel 32 is reliably positioned relative to the septal wall (e.g., within the left atrium), it may be anchored to the tissue wall via the anchor assembly 34 (i.e., positioning and deployment of the proximal anchor in abutting engagement with the septum within the right atrium), thereby eliminating the flow or shunting of blood through the opening or passageway.

Referring now to FIGS. 3-9, a variety of linkages 44 are illustrated for the occluder panel/anchor assembly. Each of these structures provide resilient directional translation and rotation for one half of the device with respect to the other. The key consideration is the responsiveness of the occluder panel 32 with and to, the anchor assembly 34 during engagement of the occluder panel 32 with the tissue opening.

The linkage 44 may take the form of extra winds on conjoint eyelets 46 (FIG. 3) and the eyelets may be enlarged. The linkage may include one or more fibers of material such as a suture or wire (FIG. 4-9). The suture may be a wire suture and may be made of Nitinol. The linkage 44 may more particularly include a wire structure such as a loop, coil, or spring, such as a coil spring or a leaf spring. The linkage 44 may have opposing ends terminating in loops or eyelets to facilitate connection to each of the halves of the device. Furthermore, greater than one linkage may be provided between the occluder panel 32 and the anchor assembly 34 (FIG. 7, see also FIG. 1 in which the anchor assembly is configured similarly to the occluder panel).

Figure 10A:
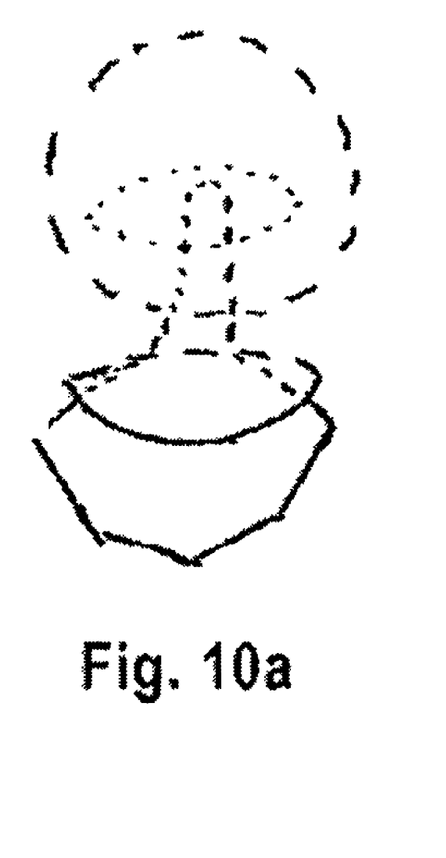
FIG. 10A is a plan view of the device of FIG. 10.
Figure 11:
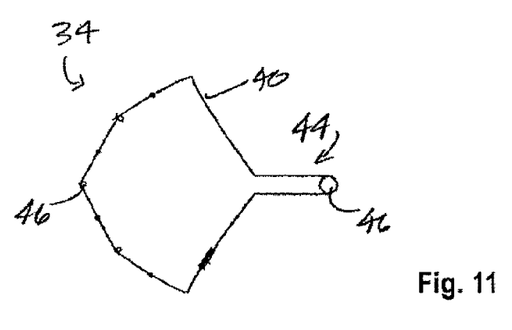
FIG. 11 illustrates the anchor structure of FIG. 10A.

Referring now to FIGS. 10 and 10A, an alternate configuration for the tissue opening occlusion device 30 of the subject invention is illustrated in a fully deployed condition, fully engaged with portions of a tissue wall adjacent an opening or passage therethrough (e.g., foramen ovale) so as to effectively block blood flow through the passage. The reversibly deployable tissue opening occluder 30 generally includes first and second halves, more particularly, an occluder panel 32 and an anchor assembly 34 extending therefrom. The occluder panel 32 includes a fabric support structure 36 and fabric 38 (not shown in FIGS. 10 and 10A) supported by a perimeter thereof. Preferably, but not necessarily, the occluder panel 32 may embrace the panel styles previously noted. As will be later detailed, once the occluder panel 32 is reliably positioned relative to the septal wall, it may be anchored to, or at least relative to, the tissue wall via the anchor assembly 34, thereby eliminating the flow or shunting of blood through the opening or passageway. According to one embodiment illustrated at FIG. 10, the occluder panel 32 has a first portion configured to engage the septum primum along a portion of the septum primum opposite the substantially planar anchor engaged within the PFO tunnel, with the septum primum being located between the occluder panel and the substantially planar anchor, and a second portion of the occluder panel configured to engage a portion of the septum secundum.

The anchor assembly 34 of FIGS. 10-23 generally includes a wire anchor element 40 of generally planar configuration adapted to be selectively manipulatable in furtherance of positioning and securing the occluder panel 32 at a tissue opening situs. The wire anchor element 40, as shown, is intended to be positioned and retained within a characteristic "tunnel" of the PFO, as for instance by expansion of the structure into tensioned engagement with portions of the tunnel. The wire anchor element 40, as will be later discussed in detail, is at least indirectly linked to a central portion 42 of the fabric support structure 36, the occluder panel 32 and anchor assembly 34 being urged toward only one of a first or a second opposite end of the occluder panel. The occluder panel 32 and the anchor assembly 34 are thereby opposingly urged into engagement with the tissue opening in furtherance of closure of the tissue opening or passage. As will become evident, it is preferred that the wire anchor element 40 have a portion configured to snugly fit against a portion of the tissue wall, and that at least a portion of the wire anchor element 40 be wide enough to anchor or set the occluder panel 32 in place despite the forces being applied to the device generally by the fluid running through the structure (e.g., heart, vessel, etc.) in which the device is placed. It is to be further understood that the wire anchor element 40 may itself be a fabric support structure (i.e., function to suspend fabric from at least a perimeter thereof), to the extent that the addition or inclusion of fabric is advantageous in furtherance of "setting," in a long term sense, the anchoring assembly (i.e., pseudo-assimilation of the structure to the tissue: further adherence of the structure to the tissue) post device deployment, or advantageous in immediate closure of the passage such as by clotting.

The anchor assembly 34 of the tissue opening occluder 30 further includes linkage 44 (not shown in FIGS. 10 and 10A) which joins the wire anchor element 40 to or with the occluder panel 32. This linkage 44 may be integral to the wire anchor element 40, as illustrated for instance in FIGS. 10 and 11, or may be a separate, discrete structure, see for instance FIG. 15, which is interposed between the wire anchor element 40 and the occluder panel 32. Generally, the functionality of the linkage is to permit a resilient multi-directional (i.e., in the Cartesian coordinate sense, namely the x, y, z directional senses) spacing of the device portions. It is advantageous that the wire anchor element 40 possess a high degree of freedom with respect to its motion relative to the occluder panel 32. In addition to the aforementioned x, y, and z motion, the ability to account for rotation (i.e., torsion) is desirable. It is preferable that the linkage be capable of reversible elongation. The occluder portions 32, 34 may be attached at a single point preferably at or near the center of the occluder panel 32, or, alternatively, conjoined at a plurality of discrete points, located or positioned within the bounds or adjacent the perimeter of each of the halves 32, 34 (i.e., within an area bounded by each perimeter of the physical structures 32, 34), or on the fabric 38 as applications warrant.

As an integral component of the wire anchor element 40, the linkage 44, more particularly the physical point of connection of the occluder panel 32 to the wire anchor element 40, is preferably an eyelet 46 (i.e., a loop) as shown in FIGS. 1 and 2. Similarly, the central portion 42 of the fabric support structure 36 of the occluder panel 32 preferably includes eyelet 46, or a plurality of eyelets, for engaging the linkage 44 of the anchor assembly 34. It is to be understood that as used herein, the term "eyelet" refers generally and broadly to a loop without limitation (e.g., round, elongate, angular, single, multiple (i.e., coil), etc.). In addition to convenient connection means, the eyelets impart a further resiliency or spring-like quality to the structures into which they are incorporated, thereby fortifying the cooperative action of the anchor assembly with the occluder panel.

As is appreciated with reference to the figures, the planar wire anchor element 40 preferably, but not necessarily, has a periphery that extends out into the atria when positioned in furtherance of device anchoring. More particularly, the wire anchor element 40 is oriented substantially parallel to the tissue wall. The anchor profile should be low so that tissue can grow into the implant and so that the implant does not cause flow disturbance or facilitate clot formation. It is preferred in these embodiments, that the angle of difference between the tissue wall and the wire anchor element be less than 45 degrees, but more preferably may be less than 15 degrees. This angle of difference is preferably measured from the central axis of the tissue wall.

Figure 16:
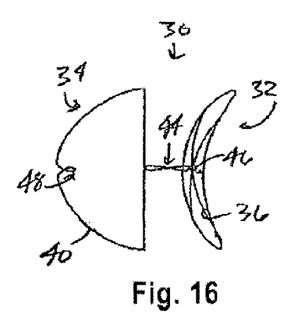
Figure 16A:
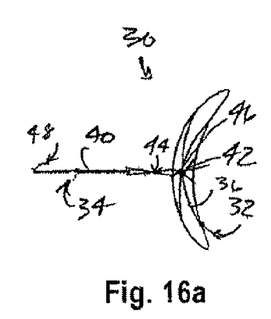
Figure 17:
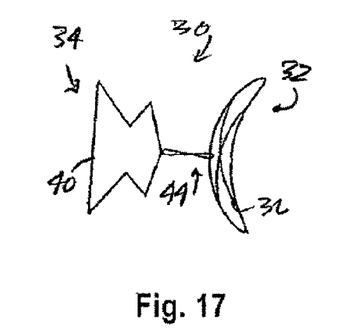
Figure 18:
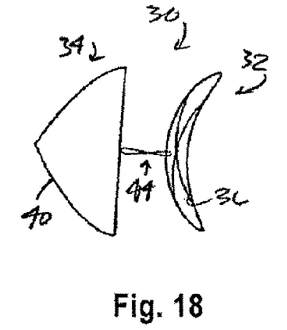
Figure 19:
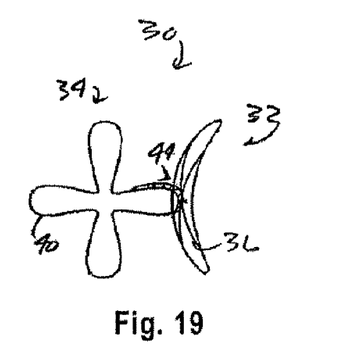
Figure 20:
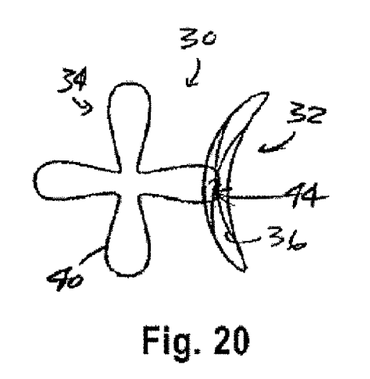
Figure 21:
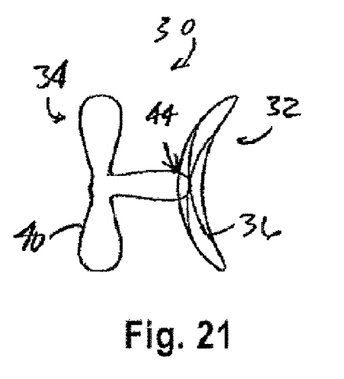
Figure 22:
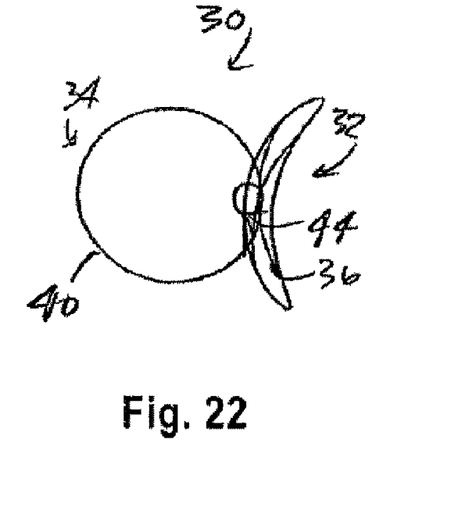
Figure 23:
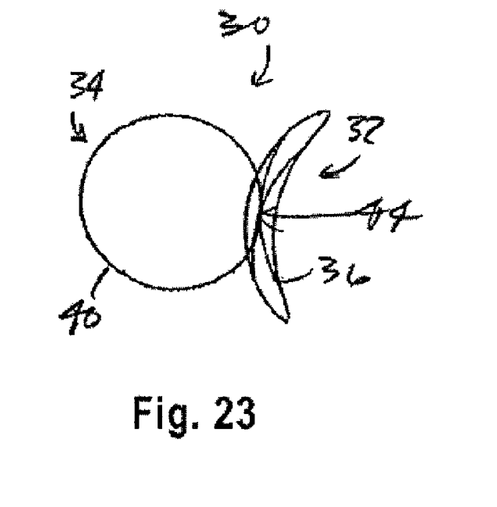

Anchor shapes are provided which offer capability to conform to the geometry of a PFO tunnel and resistance to inadvertent ejection from the tunnel in the direction of the occluder panel. The PFO tunnel generally ranges from 3-10 mm in width and 1-20 mm in length and is generally flat in height with no thickness under "at rest" conditions. Anchors such as those shown in FIGS. 12, 14, 16, 17, 21 and 22 offer superior ability to conform to different or variable tunnel widths. Further, the generally planar geometry of anchors shown in FIGS. 12-23 conform to the generally planar geometry of the PFO tunnel. Further, anchors such as those shown in FIGS. 14, 15, 17, 19 and 21 offer superior resistance to ejection from the PFO tunnel once fully or partially deployed in the tunnel due to a portion of the anchor frame being substantially parallel to the occluder panel (as shown in the figures). Finally, designs such as the anchor in FIGS. 17 and 21 provide superior accommodation of variable PFO tunnel lengths while maintaining a frame edge that, when deployed, will resist ejection from the tunnel It is further advantageous, however not necessary, that the anchor assembly 34, more particularly the wire anchor element 40, include one or more hooks 48 (e.g., FIGS. 16/16A)

for attachment of the anchor assembly 34 to the tissue wall. In devices so equipped, the portion of the wire anchor element 40 having the hook or hooks 48 formed therein, or extending therefrom, will extend substantially parallel to the tissue wall. The one or more hooks may be formed, carried and/or arranged on or with respect to the wire anchor element 40 in any suitable manner known in the art. For example, as shown in FIGS. 16/16A, the wire anchor element 40 is formed having a hook 48 on an end opposite the attachment point of the two halves 32, 34. In this case, substantially the entire wire anchor element 40 will be generally aligned along the surface of the tissue wall (i.e., in conformity therewith) when the hook 48 thereof is engaged in the wall.

As previously noted, the occluder panel 32 comprises a fabric support structure 36 and fabric 38 supported or suspended by a perimeter thereof. The fabric support structure 36 of the occluder panel 32 is generally flexible and elastically deformable. Fabric 38, which may be formed of a thin, flexible material which can be folded and pulled taut without being damaged, is suspended or otherwise affixed to the perimeter of the fabric support structures 36. It may be desirable to provide an excess of fabric to the panel 32 or the anchor 40 so as to facilitate collapse of the fabric carrying structure into a catheter.

The fabric 38 is preferably a relatively porous material. While this may seem to contradict the purpose of the device, blood will tend to coagulate on the latticework provided by the porous material. Blood flow across the tissue opening is usually substantially blocked after minimal time passage. If so desired, the fabric 38 of the occluder panel 32 may be treated with a thrombogenic agent to speed this natural process, or may be impregnated with a biocompatible polymeric compound or the like to make it relatively impervious to fluids.

The primary purpose of using a porous fabric is to accelerate the process of permanently anchoring the device in place. The support structures hold the fabric tautly and in intimate contact with the surface of the tissue wall. This intimate contact between the tissue wall and perimeter of the occluder permits ingrowth of collagen and fibrous tissue from the tissue wall into the fabric. Over time, the membrane resting against the tissue wall will become securely anchored to the wall and be covered by a layer of endothelial cells. Elastic polymeric materials such as, for example, polyester knit, nylon, polypropylene, polytetrafluoroethylene (e.g., TEFLON®), and expanded polytetrafluoroethylene (e.g., GORETEX®), as well as natural fabrics such as silk, are suitable materials for covering the fabric support structure 36 of the occluder panel 32.

To accommodate the need of the fabric support structure 36 to distort when retrieving the device 30 into a catheter, excess fabric can be provided. On an area basis relative to the support structure, an excess of fabric in the range, typically, of about 30-35 percent, and up to 50 percent, is sufficient. This range is required because the low stretch characteristics of the fabric prevent the support structure from collapsing in a manner suitable to get into the catheter. However, a 30 denier polyester knit is advantageous in that it possesses a low stretch character, is approximately 50% less bulky than known jersey style knit patterns which facilitates the use of smaller delivery catheters, and allows for the device of the subject invention to be retrieved into such catheters at forces that are not detrimental to either the catheter or the device (e.g., a 40 mm occluder may be pulled into a 12 French catheter using a reasonable peak force of about four pounds).

The fabric 38 may be attached to support structures 36, or wire anchor element 40 as the case may be, by any suitable means. For instance, the fabric 38 may be directly attached to the support structures 36 by means of an adhesive or the like, or the periphery of the fabric 38 may be wrapped about the support structures 36 and the peripheral edge attached to the rest of the fabric so as to essentially define a sleeve about the support structures 36. In the latter instance, the sleeve may fit the support structure relatively loosely so that the structure may move within the sleeve with respect to the fabric. The peripheral edge of the fabric may be affixed to the rest of the fabric sheet 38 in any suitable fashion such as by sewing. Preferably, though, the periphery of the fabric can be sewn to at least some portion of the perimeter segments of the support structures 36 using a polyester, non-adsorbable suture or the like.

The planar wire anchor element 40 and the fabric support structure 36 are preferably formed of a flexible, elastically deformable material such as a biocompatible metal, metal alloy or polymer, most preferably a superelastic material. One such material currently known in the art is a near-stoichiometric nickel/titanium alloy, commonly referred to as Nitinol or NiTi. Such superelastic materials may be elastically deformed to a much greater extent than most other materials, yet substantially fully recover their original shape when released. This permits the frame to be deformed sufficiently for insertion into, and passage through, a small-diameter catheter, yet automatically elastically return to its initial shape upon exiting the catheter.

The frame portions are preferably manufactured with nitinol wire that can be wound around the pins of a forming die and subjected to heat treatment. The wire may be bent through greater than 360 degrees to form the loops or eyelets. The ends of the wire may be attached to each other in any secure fashion, such as by means of welding, a suitable biocompatible cementitious material, or by any means known in the art. For example, the wire ends of each frame half can be connected with a titanium hypo tube using a compression crimp. Titanium is more ductile than nitinol, providing a reliable grip with excellent corrosion resistance, thereby making this method suitable for joining the ends of the material. Alternately, the preferred forms for the fabric support and/or the wire anchor element may be cut out from a sheet of such superelastic material as a single structure, by chemical etching, punching with a suitable punch and die, or any other appropriate forming method.

In order to enhance radiopacity so that the device can be viewed remotely during deployment, either the fabric support structure 36 or the wire anchor element (or both) may be provided with a radiopaque coating, such as gold or platinum. For instance, the wire may be plated with a thin layer of gold or platinum. For instance, a helically wound length of a thin radiopaque wire may be placed over the wire, alternatively, radiopaque marking bands, which are commercially available, may be employed. By placing one such band on segments of device structures, a physician can remotely visualize the frame as a plurality of small bands; when the bands are appropriately spaced from one another on a monitor, the physician knows that the frame is properly deployed. Alternatively, the fabric support structures can be made of wire with a radiopaque core.

Figures 12, 13:
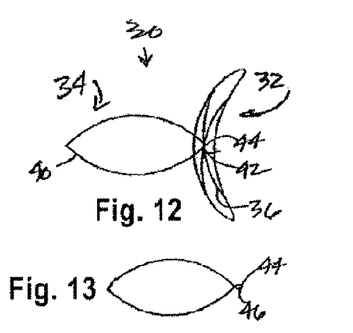
FIG. 12-23 illustrate alternate embodiments of the device of FIG. 10, FIG. 13 illustrating only the anchor portion of the device in combination with linkage structure.
Figure 14:
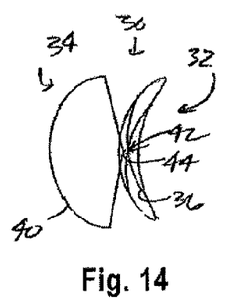
Figure 15:
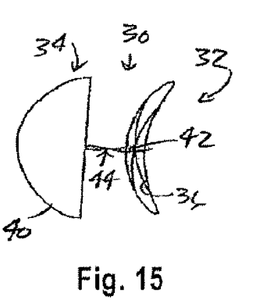

With general reference to FIGS. 12-23, alternate embodiments of the tissue opening occluder 30 of the subject invention are illustrated, more particularly numerous configurations for the anchor assemblies 34 (e.g., the planar wire anchor elements 40): an "eye" (FIGS. 12 and 13); "mushroom heads" (FIGS. 14, 15, 16, and 18); lobed elements (FIGS. 19-21); and the styles which are the subject of FIGS. 1, 2, 17, 22 and 23. The embodiments of FIGS. 15-18 show a discrete linkage 44 interposed between the occluder panel 32 and the anchor assembly 34 so as to define a non-stressed spaced apart condition for said structures.

Figure 24:
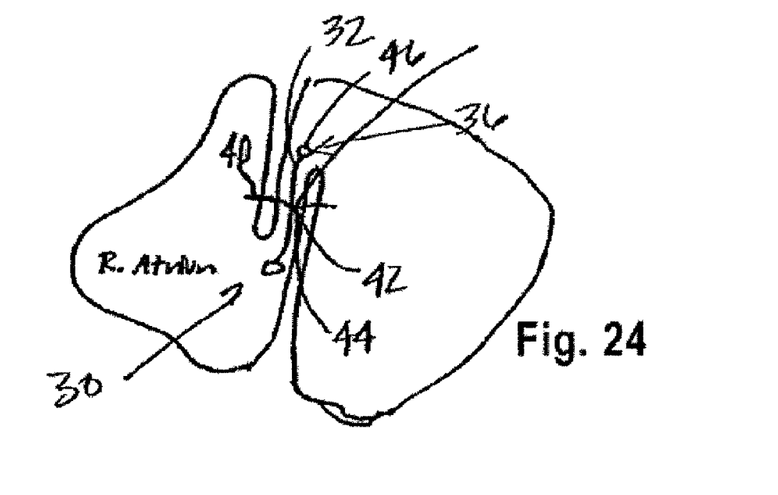
FIG. 24 illustrates yet a further embodiment of the tissue opening occluder of the present invention, in side view, in a deployed condition; and, FIGS. 25-26 illustrate embodiments of the occluder panel of FIG. 24.
Figure 25:
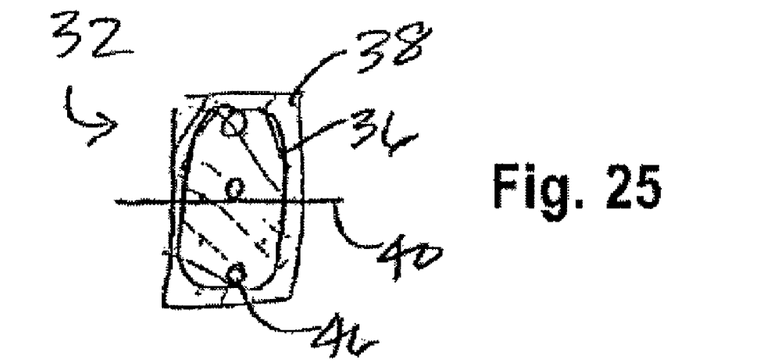
Figure 26:
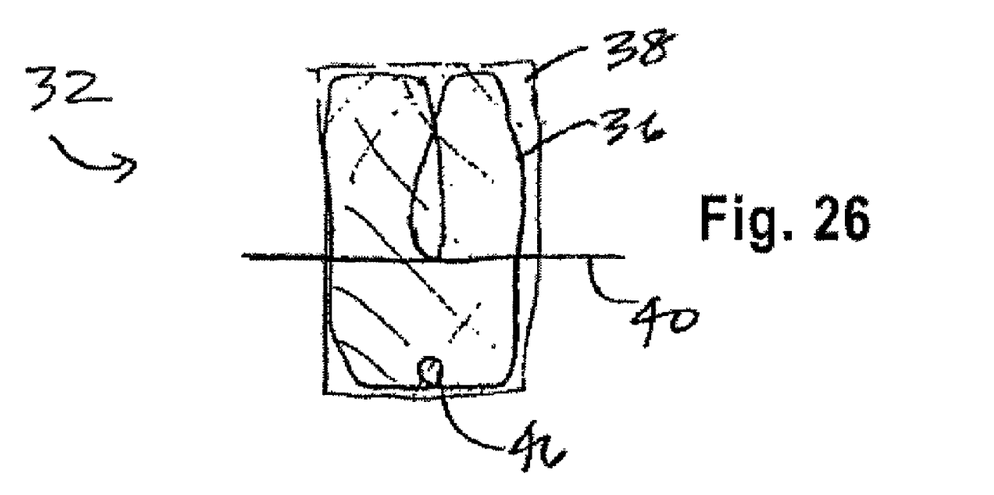

FIGS. 24-26 illustrate a further embodiment of the tissue opening occluder of the present invention in a deployed configuration. FIGS. 25 and 26 illustrate the construction of the occluder panel 32. The panel 32 includes a fabric support structure 36 which is shown as having a plurality of eyelets 46 formed therein. A fabric swatch 38 is mounted to the fabric support structure 36 in an appropriate manner such as by means of suturing (not shown).

FIGS. 25 and 26 illustrate an anchor element 40. As discussed generally herein with regard to all embodiments, upon the occluder panel 32 being deployed into position within the PFO infudibulum, the anchor element 40 can be allowed to spring into an expanded configuration in which it operatively functions to hold the occluder panel 32 in position within the infudibulum.

The anchor element 40 of FIGS. 24-26 is a generally straight wire segment which, when to be deployed from, for example, a catheter (not shown), springs to its operational configuration at least in secure engagement with heart tissue. In some instances, however, the anchor element 40 would spring into, and pass through, the heart tissue. That is the disposition illustrated in FIG. 24.

It will be understood that the fabric support structure can, in some embodiments, comprise a single continuous wire made of nitinol. A structure employing multiple nitinol sections, however, can also be utilized.

The swatch of fabric is made of any appropriate material discussed hereinbefore. In any case, the material of which it is made will function to promote tissue growth within the PFO infudibulum.

It will be understood that insertion of the occluder panel 32 into the PFO infudibulum will be accomplished in a manner known in the prior art. Typically, a nitinol fabric support structure would be positioned within a deployment catheter in a contracted configuration. After the catheter has been inserted through a patient's vasculature to arrive at the PFO, it can be deployed in an appropriate manner known in the prior art. Appropriate deployment techniques are taught in U.S. Pat. Nos. 6,214,029, 6,440,152, 6,551,344. Those techniques are hereby incorporated by reference.

Although the foregoing has focused on application of the present invention to occlude atrial PFO, the invention is not limited to occluding only foramen ovale. For instance, the instant occlusion device can be used to treat atrial septal defect, ventricular septal defect, patent ductus arteriosus, or any other congenital or acquired orificial or tubular communications between vascular chambers or vessels.

While a preferred embodiment of the present invention has been described, it should be understood that various changes, adaptations and modifications may be made therein without departing from the spirit of the invention. Changes may be made in details, particularly in matters of shape, size, material, and arrangement of parts without exceeding the scope of the invention. Accordingly, the scope of the invention is as defined in the language of the appended claims.

What is claimed is:

1. A tissue opening occluder for placement in an opening formed by overlapping septa of a patent foramen ovale (PFO), the overlapping septa forming a PFO tunnel having a substantially planar geometry with a length extending between the left atrium and right atrium of a patient and a width, the tissue opening occluder comprising:

an occluder panel configured to be positioned within one of the atria of the patient the occluder panel having a periphery and a central portion;

a substantially planar anchor with a width and a length substantially greater than a thickness thereof, and a linking element that directly connects the sub substantially planar anchor to the central portion of the occluder panel, the substantially planar anchor configured to simultaneously extend through, engage, and conform to the substantially planar geometry inside of the PFO tunnel between the left and right atria when the occluder panel is positioned in one of the atria, the length of the substantially planar anchor configured to be at least as long as the length of the PFO tunnel, and the width of the substantially planar anchor configured to be sized and conformable to fit within the width of the PFO tunnel and being sufficiently wide to anchor the occluder panel in place in one of the atria of the patient, the substantially planar structure comprising a resilient portion configured to allow the anchor to expand into tensioned engagement with portions of the interior of the PFO tunnel to secure the anchor into position in the PFO tunnel.

2. The tissue opening occluder of claim 1, wherein the substantially planar anchor comprises a wire structure.

3. The tissue opening occluder of claim 1, wherein the width of the substantially planar anchor is defined as the distance between two adjacent wire portions.

4. The tissue opening occluder of claim 1, wherein the occluder is configured such that the connection between the occluder panel and anchor is located at an edge of one of the overlapping septa.

5. The tissue opening occluder of claim 1, wherein the occluder panel is configured to be positioned in the left atrium when the substantially planar anchor simultaneously extends through, engages, and conforms to the substantially planar geometry of the PFO tunnel.

6. The tissue opening occluder of claim 1, wherein the occluder panel has a first portion configured to engage the septum primum along a portion of the septum primum opposite the substantially planar anchor engaged within the PFO tunnel, with the septum primum being located between the occluder panel and the substantially planar anchor, and a second portion of the occluder panel configured to engage a portion of the septum secundum.

7. The tissue opening occluder of claim 1, further comprising fabric on at least one of the occluder panel and the substantially planar anchor.

8. The tissue opening occluder of claim 7, wherein the fabric is porous.

9. The tissue opening occluder of claim 7, wherein the fabric is made of ePTFE.

10. The tissue opening occluder of claim 7, wherein the fabric is treated with a thrombogenic agent.

11. The tissue opening occluder of claim 7, wherein the fabric is positioned within the PFO tunnel to promote tissue ingrowth within the PFO tunnel.

12. An anchor for placement in an opening formed by overlapping septa of a patent foramen ovale (PFO), the overlapping septa forming a PFO tunnel with a length extending between a first atrium and a second atrium and a width, the area between the overlapping septa defined by the length and the width being substantially planar, the anchor comprising:

a substantially planar structure defining a length and a width substantially greater than a thickness thereof, the substantially planar structure comprising a resilient portion configured to allow the anchor to expand into tensioned engagement with portions of the interior of the PFO tunnel to secure the anchor into position in the PFO tunnel;

an occluder panel having a central portion, the occluder panel configured to extend along a surface of one of the septa in one of the left and right atrium when the substantially planar structure is expanded into tensioned engagement with portions of the PFO tunnel;

a linking element that directly connects the substantially planar structure to the central portion of the occluder panel; and a fabric connected to the substantially planar structure.

13. The anchor of claim 12, wherein the substantially planar structure comprises a wire structure.

14. The anchor of claim 12, wherein the substantially planar structure comprises two adjacent wire portions, wherein the width of the substantially planar structure is defined as the distance between the two adjacent wire portions, the distance between the two adjacent wire portions being adjustable to conform to the width of the PFO tunnel.

15. The anchor of claim 12, wherein the substantially planar structure has a length configured at least as long as the length of the PFO tunnel.

16. The anchor of claim 12, wherein the fabric is porous.

17. The anchor of claim 12, wherein the fabric is made of ePTFE.

18. The anchor of claim 12, wherein the fabric is treated with a thrombogenic agent.

19. The anchor of claim 12, wherein the fabric is positioned within the PFO tunnel to promote tissue ingrowth within the PFO tunnel.

* * * * *

UNITED STATES PATENT AND TRADEMARK OFFICE
CERTIFICATE OF CORRECTION

| | |
|---|---|
| PATENT NO. | : 7,887,562 B2 |
| APPLICATION NO. | : 11/927448 |
| DATED | : February 15, 2011 |
| INVENTOR(S) | : Michelle M. Young et al. |

Page 1 of 1

It is certified that error appears in the above-identified patent and that said Letters Patent is hereby corrected as shown below:

In column 1 at line 49, Change "problems-wherein" to --problems wherein--.

In column 1 at line 60, Change "negative," to --negative--.

In column 3 at line 49, Change "FIG." to --FIGS.--.

In column 4 at line 63, Change "(FIG." to --(FIGS.--.

In column 5 at line 7, Change "for" to --of--.

In column 5 at line 10, Change "therethrough" to --therethrough,--.

In column 6 at line 64, After "tunnel" insert --.--.

In column 9 at line 1, Change "44 interposed" to --44 interposed--.

In column 10 at line 6, In Claim 1, after "the" delete "sub".

Signed and Sealed this
Twenty-seventh Day of September, 2011

David J. Kappos
*Director of the United States Patent and Trademark Office*